(12) United States Patent
Pope

(10) Patent No.: US 8,100,128 B2
(45) Date of Patent: *Jan. 24, 2012

(54) CONTRACEPTIVE SHEATH WITH INTEGRATED BEAD CONSTRUCTION

(75) Inventor: Michael Pope, Tetsworth (GB)

(73) Assignee: The Female Health Company (UK) Plc, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 12/752,350

(22) Filed: Apr. 1, 2010

(65) Prior Publication Data

US 2010/0218770 A1   Sep. 2, 2010

Related U.S. Application Data

(63) Continuation of application No. 10/394,617, filed on Mar. 21, 2003, now Pat. No. 7,726,316.

(51) Int. Cl.
| | |
|---|---|
| *A61F 6/06* | (2006.01) |
| *A61F 6/02* | (2006.01) |
| *A61F 6/04* | (2006.01) |
| *A61F 5/44* | (2006.01) |
| *A61B 19/00* | (2006.01) |

(52) U.S. Cl. ........ 128/830; 128/834; 128/842; 128/844; 128/898; 128/917; 128/918; 604/330; 604/347

(58) Field of Classification Search ............ 128/830, 128/834–835, 837, 898, 917–918; 604/330, 604/347–353; 2/167–168; 600/38–41
See application file for complete search history.

(56) References Cited

U.S. PATENT DOCUMENTS

| | | | |
|---|---|---|---|
| 899,251 | A | 9/1908 | Graham |
| 2,371,883 | A | 3/1945 | Gammeter et al. |
| 3,852,826 | A | 12/1974 | Schindler |
| 4,004,591 | A | 1/1977 | Freimark |
| 4,630,602 | A | 12/1986 | Strickman et al. |
| 4,735,621 | A | 4/1988 | Hessel et al. |
| 4,834,113 | A | 5/1989 | Reddy |
| 4,966,165 | A | 10/1990 | Anderson |
| 4,976,273 | A | 12/1990 | Hessel |
| 4,993,433 | A | 2/1991 | Reddy |
| 5,094,250 | A | 3/1992 | Hessel |
| 5,146,930 | A | 9/1992 | Richardson et al. |
| 5,168,881 | A | 12/1992 | Reddy |
| 5,193,555 | A | 3/1993 | Richardson et al. |

(Continued)

FOREIGN PATENT DOCUMENTS

DE          593216          2/1934

(Continued)

OTHER PUBLICATIONS

"Outline for Successful Prophylactic Program", The Gee Bee Company, Waterbury Connecticut, 1934 (9 pages).

(Continued)

*Primary Examiner* — Patricia Bianco
*Assistant Examiner* — Brandon Jackson
(74) *Attorney, Agent, or Firm* — McDonnell Boehnen Hulbert & Berghoff LLP

(57) ABSTRACT

A female condom and an improved method for manufacturing a female condom is disclosed. The invention provides a device that is effective in both acting as a contraceptive and inhibiting the transmission of disease during coitus. The invention employs synthetic latex in an efficient and cost effect manufacturing method that results in an improved product.

26 Claims, 7 Drawing Sheets

U.S. PATENT DOCUMENTS

| | | | |
|---|---|---|---|
| 5,195,537 A | 3/1993 | Tillotson | |
| 5,318,042 A | 6/1994 | Gray | |
| 5,338,565 A | 8/1994 | Shlenker et al. | |
| 5,486,322 A | 1/1996 | Fuchs | |
| 5,490,519 A | 2/1996 | Hessel | |
| 5,490,525 A | 2/1996 | Reddy | |
| 5,515,862 A | 5/1996 | Artsi et al. | |
| 5,603,802 A | 2/1997 | Kruczynski et al. | |
| 5,622,185 A | 4/1997 | Richardson et al. | |
| 5,623,945 A | 4/1997 | Shecterle et al. | |
| 5,623,946 A | 4/1997 | Hessel | |
| 5,687,741 A | 11/1997 | Torger | |
| 5,695,585 A | 12/1997 | Kruczynski et al. | |
| D419,233 S | 1/2000 | Brodie | |
| 6,031,042 A | 2/2000 | Lipinski | |
| 6,341,607 B1 | 1/2002 | Couvreur | |
| 6,775,848 B2 | 8/2004 | Mcglothlin et al. | |
| 6,828,387 B2 | 12/2004 | Wang et al. | |

FOREIGN PATENT DOCUMENTS

| | | |
|---|---|---|
| DE | 3880859 | 2/1988 |
| DE | 210413 | 9/2009 |
| JP | 46-44895 | 5/1972 |
| JP | 60-156456 A | 8/1985 |
| JP | 63-216562 A | 9/1988 |
| JP | 64-22251 A | 1/1989 |
| JP | 02-504403 T | 12/1990 |
| JP | 09-505612 T | 6/1997 |
| JP | 10-513367 T | 12/1998 |
| JP | 11-507413 T | 6/1999 |
| JP | 2000-504614 T | 4/2000 |
| JP | 2000512684 | 9/2000 |
| JP | 2002528659 | 9/2002 |
| JP | 2003-521997 T | 7/2003 |
| JP | 2006070942 | 3/2006 |
| WO | 97/30668 | 8/1997 |
| WO | 97/48765 | 12/1997 |
| WO | 00/25840 | 5/2000 |
| WO | 01/90236 A | 11/2001 |

OTHER PUBLICATIONS

International Search Report for PCT/GB03102503 mailed Nov. 14, 2003.

CONTRACEPTIVE SHEATH WITH INTEGRATED BEAD CONSTRUCTION

CROSS-REFERENCE

This application is a continuation of U.S. patent application Ser. No. 10/394,617 filed on Mar. 21, 2003, the disclosure of which is incorporated by reference, now U.S. Pat. No. 7,726,316.

FIELD OF INVENTION

This invention relates to a tubular protective device or sheath for protection against the transfer of infectious matter during sexual intercourse. More particularly, the invention relates to a thin walled tubular protective device having a closed end and an open end wherein the device has a integral bead at its open end.

BACKGROUND OF THE INVENTION

Condoms are devices that are used for both contraception and protection during sexual intercourse against the transfer of infectious matter such as bacterial and viral microbes that cause venereal diseases. The continued increase in the incidences of HIV/AIDS has caused various health organizations to encourage people to increase the use of condoms during sexual intercourse in or to prevent the further spread of the disease.

Condoms comprise a thin tubular casing that is typically manufactured from natural rubber latex and that has an open end and a closed end. Traditional condoms are drawn over the penis before coitus. The casing of the condom has an inner diameter that is selected so that the condom fits tightly on the penis. At the open end of a condom an elastic, flexible ring or rolled portion of latex is usually provided. This ring portion is generally the same diameter as the tubular casing of the condom. This elastic ring portion serves primarily to secure the condom on the penis and to prevent leakage of semen for the interior of the condom. These elastic ring portions of a condom do not radially extend the open end of the condom. Indeed, the rings do not supply enough rigidity to alter the shape of the condom.

It is generally accepted that HIV/AIDS can only be transferred through contact with the carrier's bodily fluid. During sexual intercourse such a transfer of HIV/AIDS occurs when skin lesions of the carrier contact the mucous membrane or skin of the carrier's partner or through transfer of the carriers semen. Such a transfer of HIV/AIDS may occur at the base of the penis and at the vulva. There is a risk that lesions in these areas can be caused to bleed during sexual intercourse. When using a standard condom, these areas are unprotected or unshielded by the condom, and consequently a condom does not offer full protection against the transfer of infectious matter such as HIV/AIDS.

Numerous attempts have been made to design a condom or condom-like device that provides effective contraception and/or more protection against the transfer of infectious matter than the standard condom. A sampling of these attempts are described below.

An article, "Outline For Successful Prophylactic Program" (Waterbury, Conn.: The Hemingway Press, 1934), the Gee Bee Company, 7-16, discloses a prophylactic device entitled, "The Gee Bee." This device is a loose fitting tubular prophylactic having a grooved outer ring. The grooved outer ring does not form a collar-shaped, outwardly extending portion at the open of the prophylactic. This invention does not disclose any description of a "female" embodiment having a means for retaining the closed end of the device in the vagina.

German Patent Number 210,413 to Hollmann discloses a condom-like device having an outer ring. The outer ring of this invention radially extends the opening of the condom. This invention has no means for retaining the closed end of the device in the vagina.

U.S. Pat. No. 899,251 to Graham discloses an animal breeder's bag. The bag is a condom-like device for livestock that can be used to collect semen. The bag contains a fixed inner band that is positioned at about the middle of the device. This position for the attachment of the band provides for a tube and a bag-like extension. The purpose of the band and cross strips is to collect semen in a pocket. A rubber frame can be made in various shapes, but is not disclosed as forming a collar-shaped, outwardly extending portion at the opening off the prophylactic. The band of this device is designed and positioned on the device in order to provide a semen collection bag. The band does not have a structure that is located at the closed end of the device to provide a retaining means such as is required for a "female condom".

U.S. Pat. No. 4,004,591 to Freimark discloses a birth control device. This birth control device is a female condom made of a strong rubber, plastic, or other similar material. This condom has a rigid, ring-like rim that is bent or scalloped. This rim can be a wire. The rim is not adapted to radially extend the open end of this device because this device is a hard molded material and not flexible. The cross-sectional dimensions of this condom are disclosed as being sufficiently large to easily accommodate the average width of the penis with some additional clearance space. The primary function of this device is to prevent unwanted pregnancy. This device is useful in preventing the spread of venereal disease. This device provides no means at the vulva to prevent an exchange between partners of secreted fluids that can contain infectious agents. Additionally, this birth control device is intended for use by females, but includes no means to secure or maintain the device in the vagina.

U.S. Pat. No. 4,630,602 to Stickman et al. discloses a disposable contraceptive cervical barrier. The cervical barrier of this invention is similar to standard diaphragms in size and design. This cervical barrier contains various "cavities for cells" that can hold spermicidal lubricants. These spermicidal lubricants can also be placed in numerous grooves within the body of the cervical bather. Urethane polymers are used to make the device. The cervical barrier of this invention, unlike a condom, has no tubular side walls to prevent the exchange of secretion between partners that can contain a venereal disease.

Retained sheaths or "female condoms" have been sold for some time. One type of such a device is disclosed in the Hessel et al. patents, U.S. Pat. Nos. 4,735,621, 4,976,273, 5,094,250, 5,490,519, and 5,623,946. In the principle embodiment discussed in these patents, the urethane ring at the open end of the tubular member is a separate unit from the urethane sheath itself. The sheath is then attached to the ring through for example a welding step. The Hessel patents also discuss that the ring can be formed by rolling the polymer material that forms the walls of the tubular structure from the open end, so as to foam a ring of material. This ring of material can then be kept from unrolling by heating or using an adhesive.

The Hessel patents while they mention use of natural rubber latex, never address the problems associated with such a construction. Specifically, while rolling a ring is theoretically possible it presents many challenges. Typical polymer materials used in the construction of contraceptive barriers (i.e., natural rubber latex or polyurethane) will rip upon rolling or are too sticking to be effectively rolled. Often when a material is rolled into a bead of sufficient size, air or moisture is captured in the bead and upon drying the air expands and moisture boils resulting in a rupture in the bead.

SUMMARY OF THE INVENTION

The present invention is directed to a contraceptive barrier with an integral bead and methods for its manufacture. By "integral bead" it is meant that the bead or ring at the open end of the device is constructed from the same sheet that makes up the barrier wall without any additional pieces. The device of the present invention is a contraceptive device that is inserted within the vagina and retained there during coitus. The device includes a barrier wall that forms a pouch. The pouch is generally tubular shaped with an open end and a closed end. The open end has a diameter greater than the pouch creating a trumpet shape or a flange at the open end. The diameter of the pouch is of a sufficient size to allow free movement of a penis during coitus. Around the outer edge of the open end is a bead that provides rigidity to the open end. The bead is an integral bead. The bead is formed by rolling the barrier wall of the pouch upon itself, until a bead of sufficient thickness to provide the needed rigidity is obtained. An adhesive material may be used to maintain the bead in the rolled position and keep it from unrolling.

The device may also include a retaining member for keeping the device within the vagina during coitus. This retaining member is generally located at the closed end of the tubular pouch. It could take on many forms including a retaining ring or sponge.

In the present invention the pouch is manufactured using a dipping process. Specifically, the present invention is preferably composed of a synthetic nitrile latex material. A former, of the appropriate shape, is dipped into a suspension of the synthetic nitrile latex to form a sheath. The sheath is then cured to allow cross linking to occur in the synthetic nitrile latex and make it sufficiently durable. Synthetic nitrile latex has the advantage of being relatively inexpensive, easy to work with and not subject to the allergic reactions often found with natural rubber latex. In addition, synthetic nitrile latex is significantly stronger than natural rubber latex and provides a better barrier against the transmission of disease. In addition, synthetic nitrile latex has a higher modulus of elasticity than prior used natural rubber latex in condoms. This means the product will form a loose fitting liner in the vagina that will stay in place during intercourse. A natural rubber latex device, being more elastic and lower modulus material, is more likely to be dislodged.

DETAILED DESCRIPTION OF PREFERRED EMBODIMENTS

Figure 1:
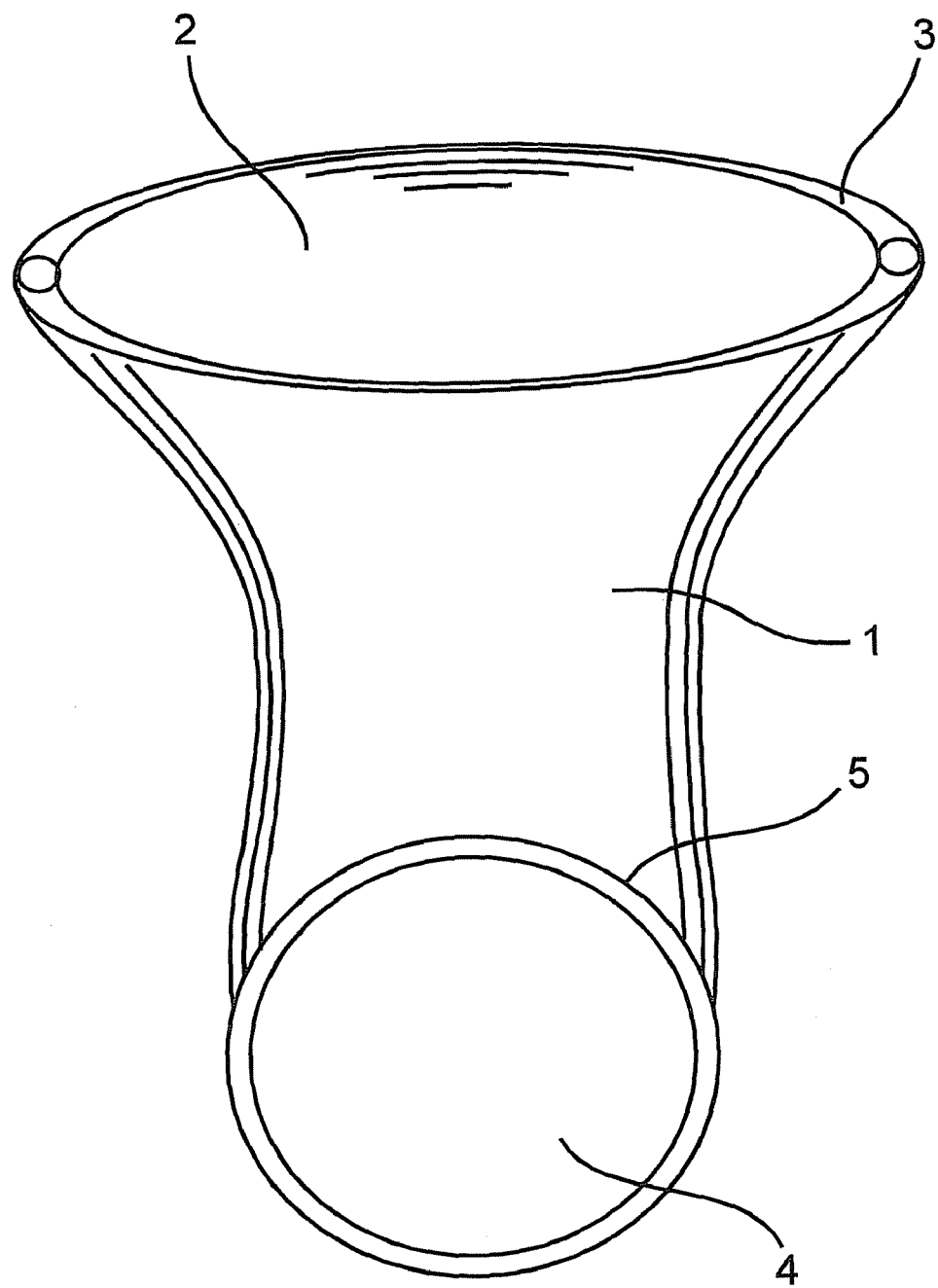
FIG. 1 is an exemplary embodiment of the present invention.

The invention relates to an improved tubular protective device, such as a female condom like device or vaginal shield, and an improved method for manufacturing it. Exemplary embodiments of various structures of the present invention are shown in FIGS. 1 and 3-7. These devices have been shown to provide protection against the transfer of infectious matter, including HIV/AIDS and venereal diseases. The protection is enhanced because the tubular protection device has at its open end an outwardly extending collar that is supported by a rigid bead or ring like structure. The bead is desirably adapted to maintain the collar of the device in a radially extended or stretched condition. As a result, the bead has to be of sufficient size and rigidity to extend the collar. The collar is preferably of a dimension that covers the vulva completely and is relatively immovable during coitus. The tubular protective device preferably has a sufficiently large inner diameter to allow movement of a penis with respect to the walls of the tubular device. The walls of the tubular device are held in a relatively immoveable state or condition within and against the vaginal wall by a retaining mechanism. In one exemplary embodiment, the retaining mechanism is a ring like member that is either removable or integrally connected to the closed end of the tubular protective device.

The flexible, thin wall tube of the invention is desirably cylindrical in shape having an open end and a closed end. The tube is preferably made of a synthetic polymer material. Particularly preferred are synthetic latex materials and in particular synthetic nitrile latex.

The wall thickness of the tubular protective device can vary. Typically, thinner wall thicknesses for the device allow more sensitivity during coitus. However, the wall thickness must be sufficient to provide the necessary strength and prevent rupture. Moreover, it is preferred that the wall thickness be uniform throughout the device, some variation in the wall thickness is however acceptable. Preferably, the wall thickness for the device is between 50 and 70 microns.

The internal or inner diameter of the tubular protective device in its unstretched state is desirably of a sufficiently large dimension to permit movement of a penis with respect to the protective device during sexual intercourse. A tubular protective device having a large inner diameter functions as a liner for the vaginal wall or as a "vaginal pouch". In this situation, the device is relatively stationary to the vaginal wall and the glans is in direct contact with the surface against which it is moving. This structural arrangement, wherein the inner diameter of the tubular protective device is larger than a penis, provides greater sensitivity for both partners.

Standards within the industry for condoms, typically, do not define the inner diameter of a condom, but define the acceptable width of the condom when it is laid flat on a surface. A condom having a width of about 47 millimeters to about 51 millimeter is considered, within the industry, to be form fitting. Contoured or loose fitting condoms have a width of about 50 millimeters to about 54 millimeters. For this invention an acceptable width is at least about 50 millimeters in an unstretched state along the entire length of the tube. A desirable range for the width of the tubular protective device of this invention is between about 55 millimeters and about 85 millimeters.

The collar-shaped, outwardly extending portion of the tubular protective device has a mechanism for radially stretching or extending the collar, such as a bead or ring-like member. Furthermore, the bead serves to prevent the open end of the tubular protective device from being pushed into the vagina during sexual intercourse. As mentioned above, this mechanism for extending the collar or ring-like member, in the most desirable embodiments of the invention, is integral to the open end of the tubular protective device and is formed from the walls of the device. Such a structure is formed by rolling the walls of the device, from the open end of the tube so as to form a ring of material. Steps should be taken to maintain the structure of this ring and prevent it from unrolling.

The diameter of the ring formed by the integral bead is desirably large enough to prevent the exchange of secretions between partners during sexual intercourse. In other words, the diameter of the ring formed by the integral bead is desirably large enough such that the vulva and the base of the penis are covered by the extended collar. The preferred embodiments of the invention have a first diameter for the tube of the device and a second diameter for the ring formed by the integral bead, wherein the second diameter is larger than the first diameter. Acceptable diameters for the ring formed by the integral bead of the device are at least about 50 millimeters and desirably between about 60 and about 75 millimeters. Preferably, the collar is conically shaped and when a tubular protective device having an inner diameter of approximately 50 millimeters is used, the collar, supported by the integral bead, preferably, has an inner diameter of approximately 70 millimeters.

The integral bead must be of sufficient size and rigidity to support the collar. As a result, the integral bead of the present invention must be significantly larger than the ring formed on a standard condom. In prior art device, a wire or plastic ring was used to provide this rigidity. The present invention eliminates the need for such a substructure.

Figure 2:
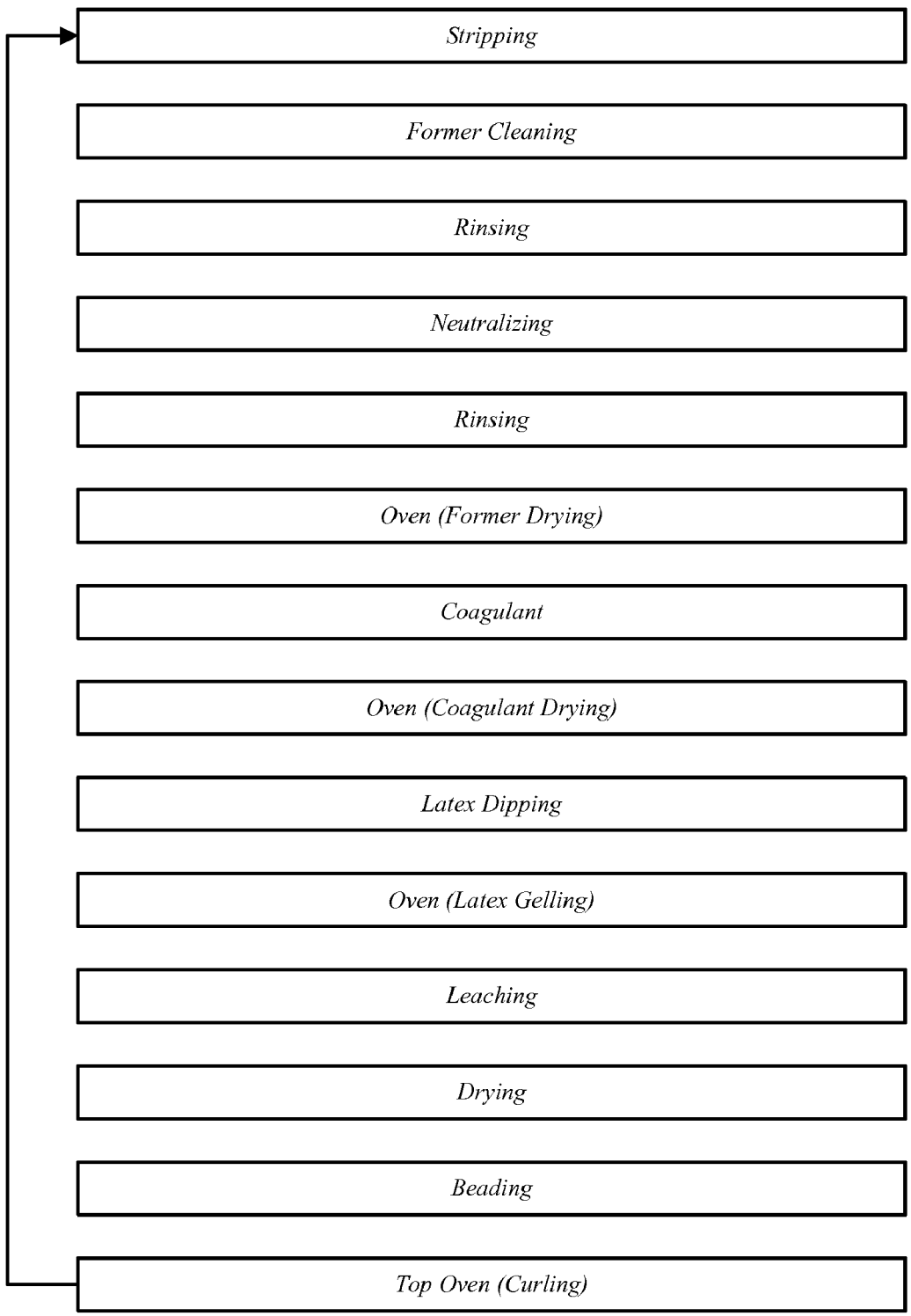
FIG. 2 is a flow chart illustrating a portion of the process used to manufacture the structure of the present invention.

An embodiment of the manufacturing process for forming the product of the present invention is set forth in FIG. 2. In this exemplary process, the tubular device is manufactured by first dipping a preheated (70° C.) former (preferably ceramic) into a coagulant, such as calcium nitrate ($CaNO_3$). Then the former, coated with the coagulant, is dried. The dried former is then dipped into a heated aqueous suspension of synthetic latex polymer material. The coagulant allows the synthetic latex to better form on the former. The synthetic latex is then dried in an oven until substantially dry. In an exemplary embodiment, the material is then leached in water. After the leaching process it is allowed to air dry. The synthetic latex is then cured. After the synthetic latex is cured, the open end of the tubular device is rolled upon itself to form the integral bead. The bead is rolled to a substantial size in order to provide the rigidity. The integral bead is at least about 3-3.5 millimeter in cross section diameter. In general, this entails rolling about 130 to 190 millimeters of the tubular device upon itself. In one exemplary embodiment, at the last roll of the bead an adhesive is applied to the outer wall of the tubular device and rolled up into the bead. This adhesive keeps bead from unrolling. While any appropriate adhesive material could be used, in a particular embodiment the adhesive is the same synthetic latex that is used to form the tubular device. If the synthetic latex is used as the adhesive, it is advantageous to then further cure the device for a second time.

In another exemplary embodiment the use of an adhesive may be avoided. In this embodiment the first cure of the synthetic latex is done at a temperature and for a time that allows only a partial cure, such that synthetic polymer retains the ability to bond with itself. The bead is then formed by rolling the open end of the tubular device upon itself. The device is then cured for a second time, completing the curing process, resulting in cross-linking within the bead and preventing it from unrolling.

Insertion into the vagina of the tubular protective device of the invention can be done by either the man or the woman. The device can be inserted in the traditional manner wherein the male partner places the device over the penis before coitus. The female partner can insert the device by hand or by means of an insertion probe or applicator.

The tubular protective device has structure that prevents the unintentional removal or from slipping out of the device from the vagina once insertion into the female partner has occurred. Prevention of unintentional, removal is accomplished by a mechanism for retaining the device in the vagina. The mechanism for retaining can be fashioned in a variety of structures, but is desirably a circular elastic member such as an elastic ring. This member or ring can be placed internal or external to the wall at or essentially at the closed end of the tubular protective device. After being placed correctly in the vicinity of the uterus, the circular elastic member or elastic ring is maintained within the vagina in the same manner as a diaphragm.

The mechanism for retaining the tubular device in a vagina can comprise one of many structures that are fixed or removable. Ring-like members can provide suitable mechanisms for retaining as discussed above. Ring-like members are made more suitable for use as retaining mechanisms when at least one segment of the ring is removed. Such embodiments, having a ring with an open segment, permit the ring-like member to be pinched or partially collapsed for easy insertion into the vagina. An open or collapsible retaining mechanism can be desirable in embodiments wherein the mechanisms for retaining is other than a ring-like member. Such embodiments can be in the form of ribs that are longitudinally molded into or extruded onto the closed end of the device as well as cap-like retaining mechanisms. Circular sponges located at the closed can also be effective retaining mechanism. Regardless of the structure adopted for the retaining mechanism, the retaining mechanisms must be structured such that it does not weaken the wall of the tubular protective device nor interfere with coitus, In one exemplary embodiment, the retaining mechanism is a ring made of an elastic material that softens when heated to body temperature such as a polyurethane material. The ring is placed, unattached, at the closed end of the tubular device. The ring is of a size to hold the wall of the tubular device against the wall of the vaginal cavity. The internal diameter of the ring is of sufficient size so as not to interfere with coitus. The fact that the ring softens at body temperature facilitates the removal of the device.

Insertion of the tubular protective device into the vagina can be facilitated by enclosing the closed end of the device in a sheathing which is axially movable relative to the tubular protective device. During the insertion of the tubular protective device into the vagina, the sheathing is moved backwards and, thus, opens for insertion of the closed end of the tubular protective device. Such a sheathing is not typically present if a means for retaining the device in the vagina, such as an elastic ring, is present.

A lubricant is, desirably, applied to the tubular protective device prior to or in connection with the insertion of the tubular protective device. The lubricant is applied at least to the inner side of the device in order to reduce friction during contact with the penis. If desired, a lubricant can also be applied to the exterior side of the device. Application of a lubricant to the exterior side of the tubular protective device can facilitate the insertion of the device into the vagina.

Selection of a desirable lubricant can vary greatly. The selection of a lubricant depends, in part, upon the compatibility of the lubricant with the polymer synthetic latex used to manufacture the device. Desirable lubricants can include ointments, creams, or water-based mucilages or mucilage-like substances such as cellulose-based lubricants.

The invention is described in more detail with reference to the figures that show desirable embodiments of the tubular protective devices according to the invention.

FIG. 1 is a tubular protective device according to the preferred embodiment of this invention. The tubular protective device 1 has an open end 2. The open end 2 has an integral bead 3. A closed end 4 of the tubular protective device has an retaining ring 5. In this embodiment the retaining ring 5 is placed unattached in the closed end 4 in a plane transverse to the integral bead 3. The integral bead 3 is constructed entirely from rolling of tubular wall upon itself.

Figure 3:
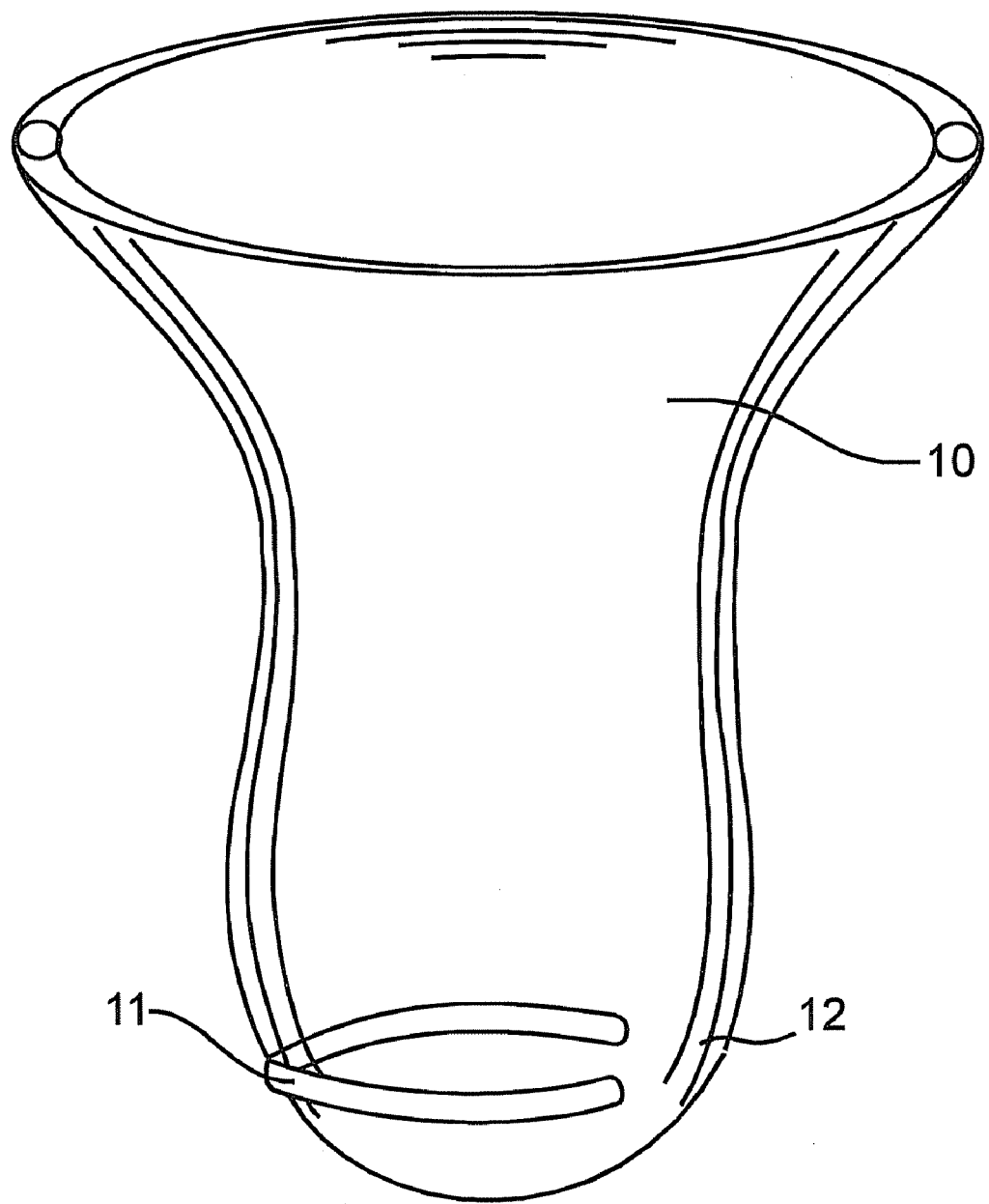
FIG. 3 is another exemplary embodiment of the present invention with a modified retention ring.

FIG. 3 is an alternative embodiment of a tubular protective device 10 according to this invention. A ring-like member 11 is a fixed to the closed end of the tubular protective device 10. The ring-like member 11 has an open segment 12 for collapsing the ring-like member in order to facilitate insertion of the closed end of the tubular protective device.

Figure 4:
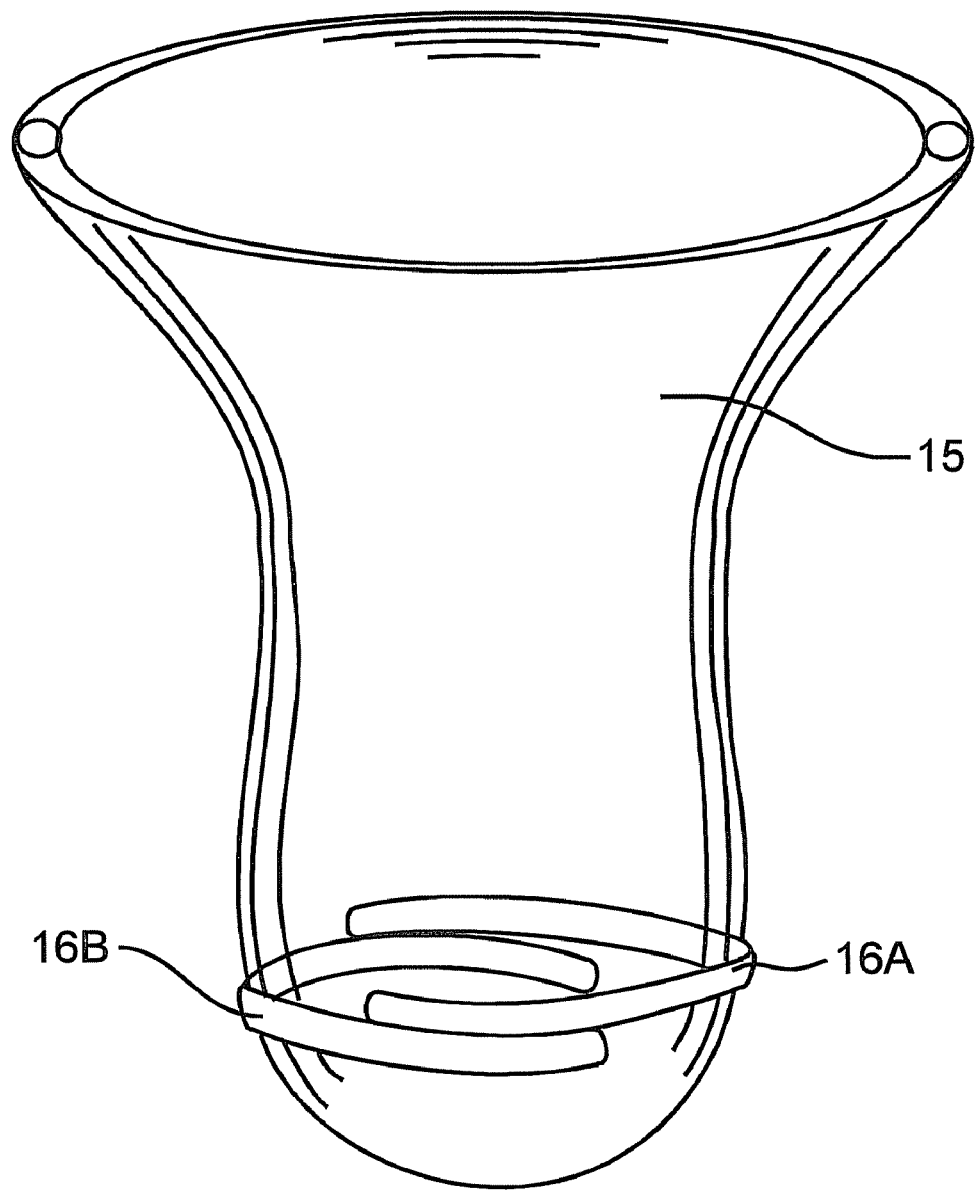
FIG. 4 is yet another exemplary embodiment of the present invention with a further modified retention ring.

FIG. 4 is an alternative embodiment of a tubular protective device 15 according to this invention. This embodiment has two "opposing" crescent-shaped, ring-like members 16A and 16B. Ring-like members 16A and 16B can be compressed, but provide uniform radial extension of the closed end of the tubular protective device 15. The uniform radial extension is desirable in order to ensure that the closed end is properly seated in the vagina in the same manner that a diaphragm is worn. Additionally, the ring-like members 16A and 16B provide a "ribbed effect" for the tubular protective device 15. It is important to know that the terminal portion of the present ring-like members 16A and 16B are softly roundly so as to prevent uneven stress on the wall of the tubular protective device 15 or interference with coitus.

Figure 5:
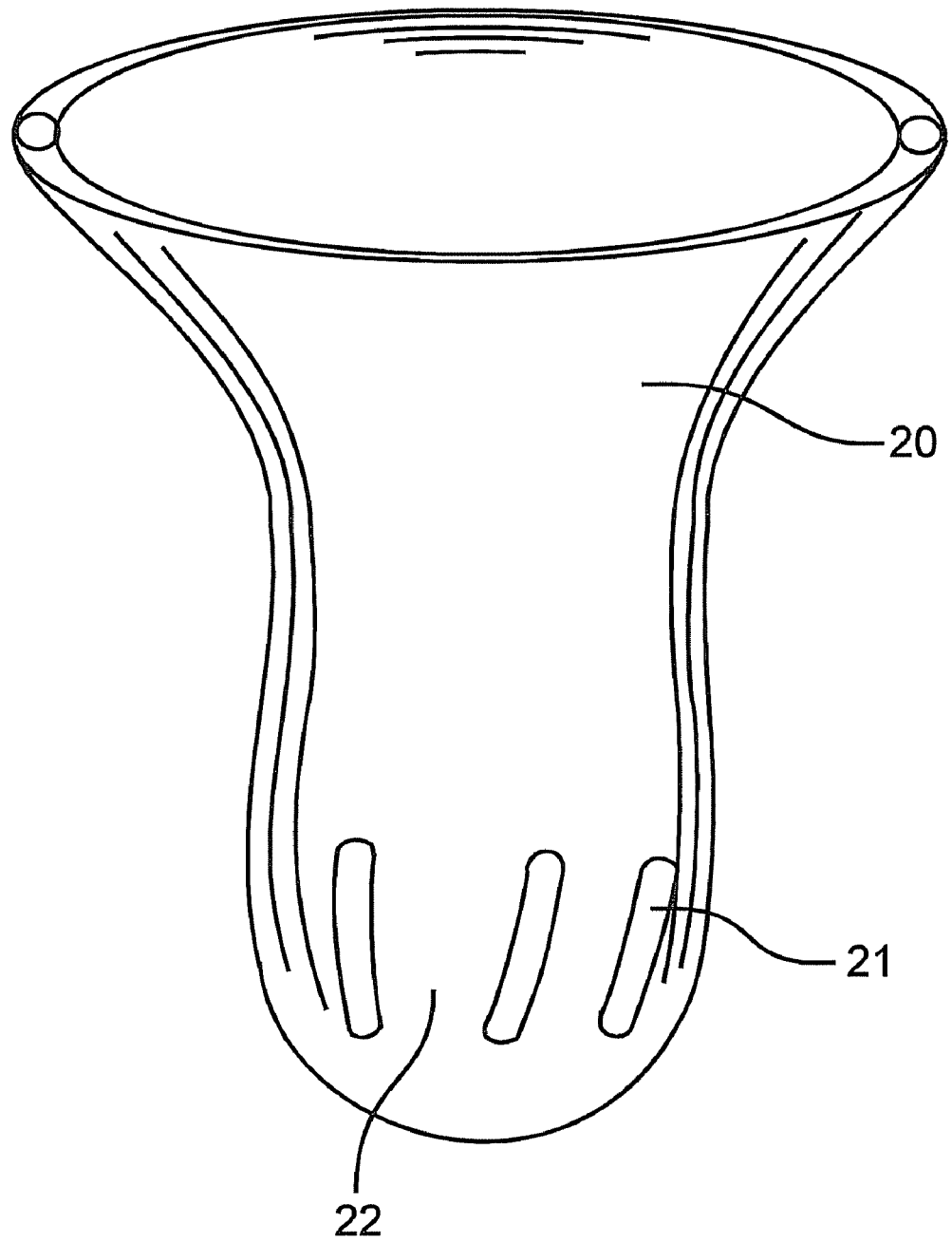
FIG. 5 is still another exemplary embodiment of the present invention with a modified retention ring.

FIG. 5 is an alternative embodiment of a tubular protective device 20 according to this invention. The closed end of this embodiment of the invention has longitudinal segments 21 positioned at the closed end to provide a means for retaining the tubular protective device 20. Desirably, these longitudinal segments 21 are molded or extruded to have a slight curvature along the longitudinal axis of the tubular protective device 20. This curvature enables the longitudinal segments 21 to radially extend the closed end of the tubular protective device 20. The spaces 22 in between the longitudinal segments 21 enable the closed end to be compressed for insertion into a vagina.

Figure 6:
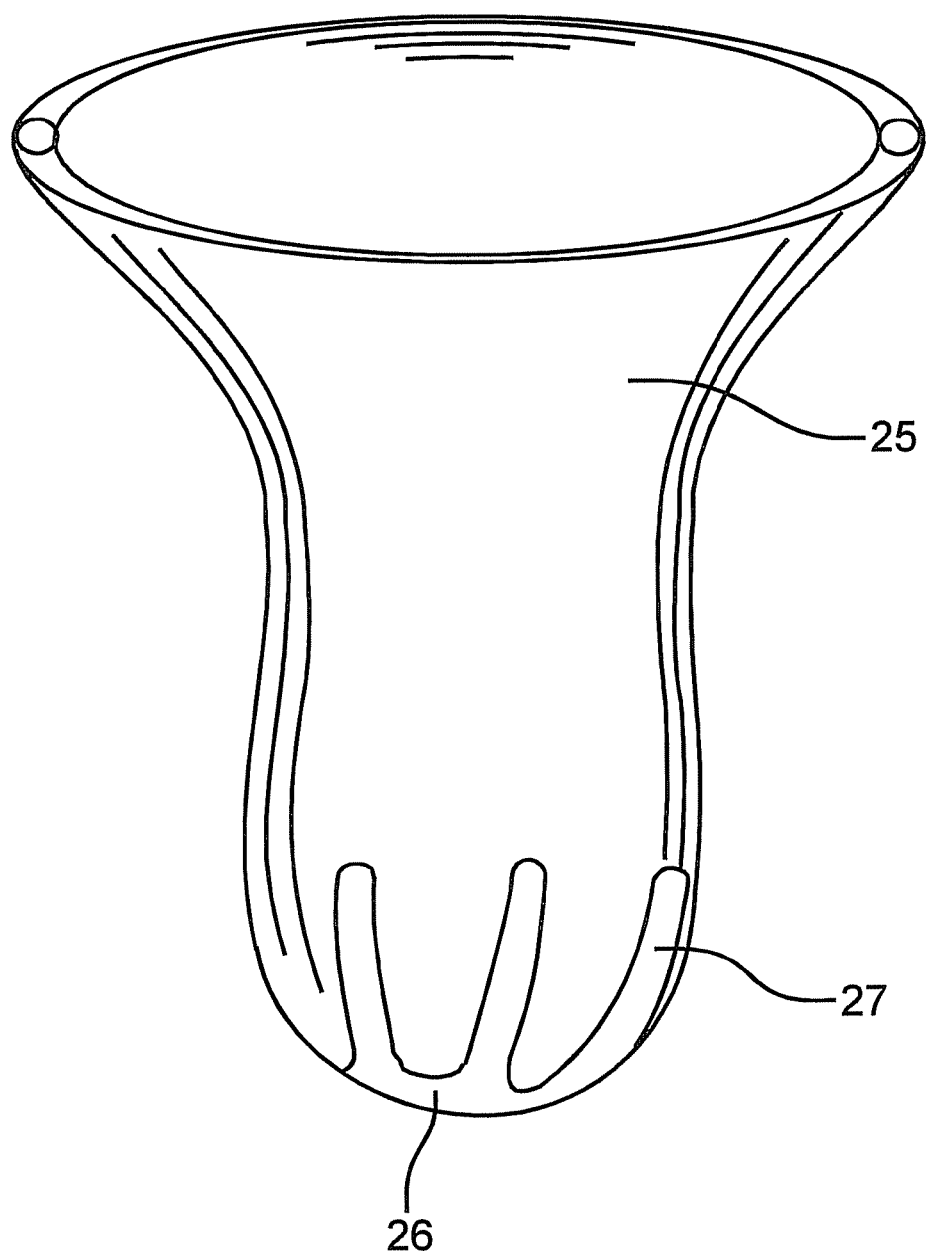
FIG. 6 is again another exemplary embodiment of the present invention with a modified retention member at the closed end of the sheath.

FIG. 6 is an alternative embodiment of a tubular protective device 25 according to this invention. The closed end of this device has a star-shaped retaining means 26. The star-shaped retaining means 26 has a plurality of longitudinal extensions 27 which radially extend the closed end of the tubular protective device 25.

Figure 7:
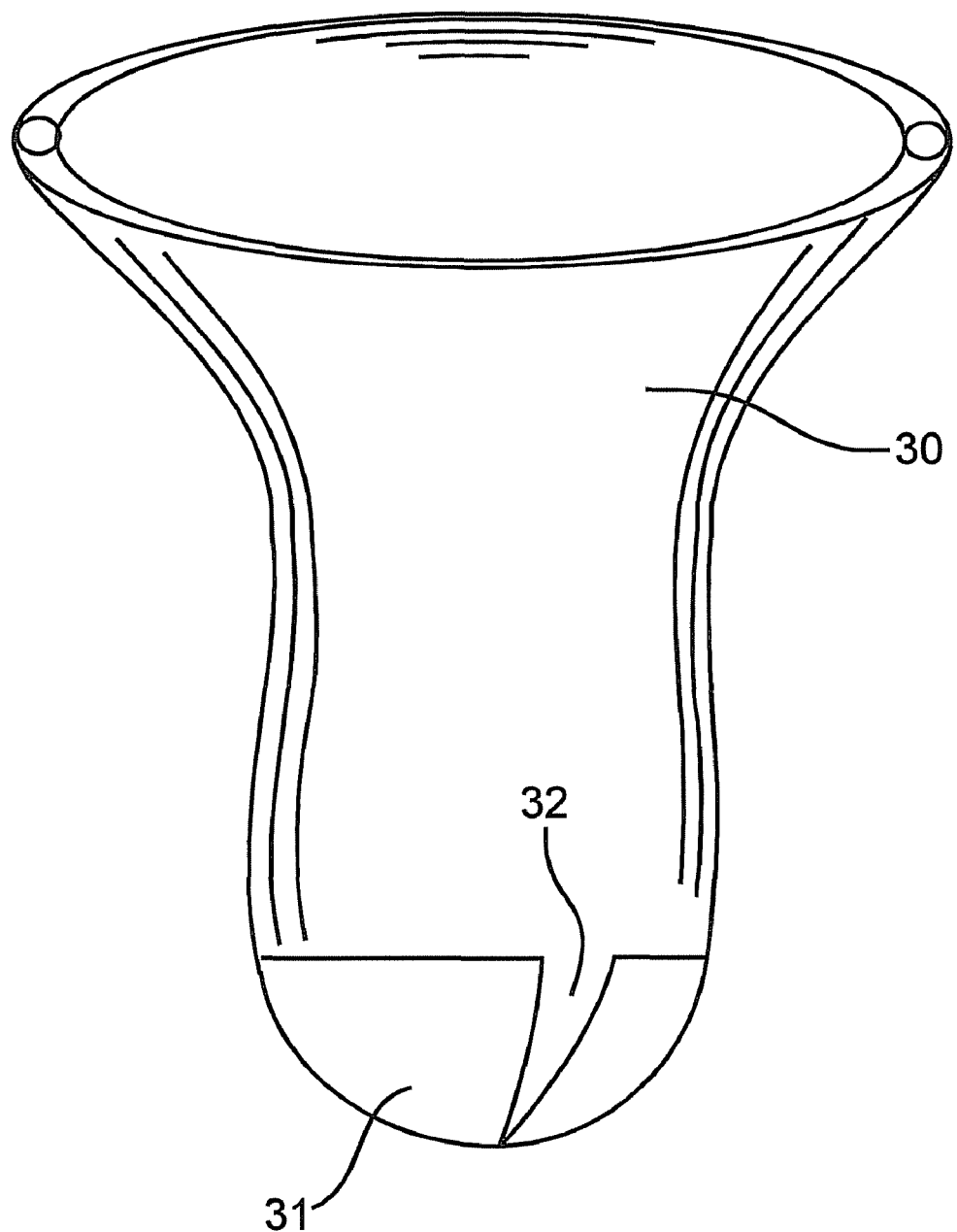
FIG. 7 is another exemplary embodiment of the present invention with a further modified retention member at the closed end of the sheath.

FIG. 7 is an alternative embodiment of a tubular protective device 30 according to this invention. This embodiment has a cap-like portion 31 at the closed end of the tubular protective device 25. Cap-like portion 31 has an open segment 32 which can be compressed together for easy insertion of the closed end of the tubular protective device 30. The cap-like portion 31 provides an effective retaining means, but its thickness can interfere with coitus during use of the tubular protective device 30. The cap-like portion 31 can, optionally, have a plurality of open portions 32.

Manufacture of the tubular protective device, consistent with the process set forth in FIG. 2, is further described by the following example:

EXAMPLE 1

Initially a synthetic latex compound is compounded in a conventional manner. The compounding step consists of mixing latex concentrate with stabilizer and a chemical dispersion agent in order to create a homogeneous substance appropriate for manufacturing the invention. A ceramic former in the desired shape is cleaned and pre-heated at 70° C. for at least thirty minutes. The pre-heated former is dipped in to a coagulant (such as $CaNO_3$) with about zero dwell time such that the surface of the former is coated with the coagulant. Care should be taken to ensure that the layer of coagulant is uniform over the surface of the former. The coagulant coated former is then dried in an oven for about one to two minutes at 120° C. to 130° C. Once dry, the former is dipped in a suspension of synthetic latex (zero dwell time) at 26° C.-30° C. The synthetic latex coated former is then removed and dried in an oven at 90° C. for about three minutes. This drying process may result in a partial cure of the synthetic latex on the former. The latex coated former is then leached in water two to three minutes at a temperature of 65° C. This leaching removes residual soluble material from the product. The leaching solution may include a biocide suspension in the water to further eliminate any potential germs. After leaching the synthetic latex coated former is allowed to dry at ambient temperature.

The integral bead is then formed by rolling the open end of the synthetic latex upon itself while on the former. The former may be adopted with an annular groove to receive the bead when formed. A strip of wet synthetic latex may be applied to outside of sheath at the bottom of the integral bead. The integral bead is then rolled to encompass the wet synthetic latex. The device is subjected to a second cure for about 15 minutes at 95° C. to 120° C. This second cure creates cross linking bonds in the synthetic latex and both secures the bead an toughens the material.

After the second cure the device is removed from the former. A polyurethane ring may be place is the closed end of the device. The product is then leak tested, lubricated and readied for packaging.

CONCLUSION

The present invention represents an improvement in both the structure and the methods for manufacturing female condoms. The present invention provide a device that less expensive to manufacture while maintaining a high quality product. The invention overcomes the issues experience in the prior art that resulted in inefficient and ineffective manufacture of female condoms.

I claim:

1. A method for manufacturing a female condom comprising:
    dipping a former into a container of synthetic nitrile latex such that the synthetic nitrile latex forms a coating on the former, said coating defining a tubular wall with an open end and a closed end;
    drying the coating on the former;
    partially curing the coating on the former;
    after the partial curing, rolling the open end of the tubular wall upon itself to form an integral bead wherein the integral bead is of a diameter greater than that of the tubular wall; and complete curing the coating after the integral bead is formed.

2. The method of claim 1 further comprising the step of inserting a retaining mechanism into the closed end of the tubular wall.

3. The method of claim 2 wherein the retaining mechanism comprises an elastic ring like member.

4. The method of claim 3 wherein the ring like member is made of polyurethane or similar elastomeric material.

5. The method of claim 3 wherein the ring like member is only a portion of a circle.

6. The method of claim 1 further comprising the steps of coating the former with a coagulant before dipping it into the synthetic nitrile latex and drying the former once coated with the coagulant.

7. The method of claim 6 wherein the coagulant is calcium nitrate.

8. The method of claim 1 wherein the integral bead has a cross section diameter of greater than 3 mm.

9. The method of claim 1 wherein the integral bead consists of at least 130 mm of the tubular wall.

10. The method of claim 1 wherein adhesive material is applied to the outer portion tubular wall such that the bead is rolled over the adhesive and the adhesive material inhibits the bead from unrolling.

11. The method of claim 1 wherein the cure step is done at least 95° C. for at least about 15 minutes.

12. The method of claim 1 further comprising the steps of:
leaching the tubular wall after the drying step and before the partial cure and drying the tubular wall after the leaching step.

13. The method of claim 6 wherein the former is preheated to at least about 70° C before coating it with the coagulant.

14. A method for manufacturing a female condom comprising:
dipping a former into a container of curable polymer material such that the curable polymer material forms a coating on the former, said coating defining a tubular wall with an open end and a closed end;
drying the coating on the former;
partially curing the coating on the former;
after the partial curing, rolling the open end of the tubular wall upon itself to form an integral bead wherein the integral bead is of a diameter greater than that of the tubular wall; and
complete curing the coating after the integral bead is formed.

15. The method of claim 14 further comprising the step of inserting a retaining mechanism into the closed end of the tubular wall.

16. The method of claim 15 wherein the retaining mechanism comprises an elastic ring like member.

17. The method of claim 16 wherein the ring like member is made of polyurethane or similar elastomeric material.

18. The method of claim 16 wherein the ring like member is only a portion of a circle.

19. The method of claim 14 further comprising the steps of coating the former with a coagulant before dipping it into the curable polymer material and drying the former once coated with the coagulant.

20. The method of claim 19 wherein the coagulant is calcium nitrate.

21. The method of claim 14 wherein the integral bead has a cross section diameter of greater than 3 mm.

22. The method of claim 14 wherein the integral bead consists of at least 130 mm of the tubular wall.

23. The method of claim 14 wherein adhesive material is applied to the outer portion tubular wall such that the bead is rolled over the adhesive and the adhesive material inhibits the bead from unrolling.

24. The method of claim 14 further comprising the steps of:
leaching the tubular wall after the drying step and before the partial cure and drying the tubular wall after the leaching step.

25. The method of claim 19 wherein the former is preheated to at least about 70°C before coating it with the coagulant.

26. A female condom made by a method comprising:
dipping a former into a container of synthetic nitrile latex such that the synthetic nitrile latex forms a coating on the former, said coating defining a tubular wall with an open end and a closed end;
drying the coating on the former;
partially curing the coating on the former;
after the partial curing, rolling the open end of the tubular wall upon itself to form an integral bead wherein the integral bead is of a diameter greater than that of the tubular wall; and
complete curing the coating after the integral bead is formed.

* * * * *